US008012566B2

(12) United States Patent
Govinda Raju et al.

(10) Patent No.: US 8,012,566 B2
(45) Date of Patent: Sep. 6, 2011

(54) MICRONEEDLES FORMED BY ELECTROPLATING AND SELECTIVELY RELEASING TEMPERATURE SENSITIVE LAYERS

(75) Inventors: Ramesh Govinda Raju, Singapore (SG); Patricia A. Beck, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 966 days.

(21) Appl. No.: 11/485,504

(22) Filed: Jul. 12, 2006

(65) Prior Publication Data

US 2008/0014416 A1 Jan. 17, 2008

(51) Int. Cl.
*B32B 3/00* (2006.01)
*B32B 5/00* (2006.01)
*B41M 5/00* (2006.01)
*B44C 1/17* (2006.01)
*G03G 7/00* (2006.01)
*C25D 1/00* (2006.01)

(52) U.S. Cl. .......... 428/161; 428/98; 428/156; 428/164; 428/195.1; 428/209; 205/67

(58) Field of Classification Search .................. 174/263; 264/239; 604/239, 340; 205/67–79
See application file for complete search history.

(56) References Cited

U.S. PATENT DOCUMENTS

| 4,549,597 | A | * | 10/1985 | Hamamura | 164/35 |
|---|---|---|---|---|---|
| 5,686,119 | A | * | 11/1997 | McNaughton, Jr. | 425/130 |
| 5,953,623 | A | * | 9/1999 | Boyko et al. | 438/612 |
| 6,106,751 | A | * | 8/2000 | Talbot et al. | 264/81 |
| 6,187,210 | B1 | * | 2/2001 | Lebouitz et al. | 216/11 |
| 6,334,856 | B1 | * | 1/2002 | Allen et al. | 604/191 |
| 6,503,231 | B1 | * | 1/2003 | Prausnitz et al. | 604/272 |
| 6,520,778 | B1 | * | 2/2003 | Eldridge et al. | 439/66 |
| 6,551,849 | B1 | * | 4/2003 | Kenney | 438/34 |
| 6,623,457 | B1 | * | 9/2003 | Rosenberg | 604/191 |
| 6,743,211 | B1 | * | 6/2004 | Prausnitz et al. | 604/239 |
| 6,749,792 | B2 | * | 6/2004 | Olson | 264/328.1 |
| 6,816,385 | B1 | * | 11/2004 | Alcoe | 361/767 |
| 6,909,054 | B2 | * | 6/2005 | Sakamoto et al. | 174/260 |
| 2002/0155737 | A1 | * | 10/2002 | Roy et al. | 439/66 |
| 2004/0045642 | A1 | * | 3/2004 | Bonet | 148/528 |
| 2004/0146611 | A1 | * | 7/2004 | Arias et al. | 426/106 |
| 2005/0008821 | A1 | * | 1/2005 | Pricone | 428/131 |
| 2005/0011858 | A1 | * | 1/2005 | Kuo et al. | 216/17 |

OTHER PUBLICATIONS

Chapter 14 of Intel Packaging Databook. "Ball Grid Array (BGA) Packaging." Published 2000. Intel. http://www.intel.com/design/packtech/packbook.htm.*
Ask a Scientist Chemistry Archive. "Soldering Flux." Published May 2004. United States Department of Energy. http://www.newton.dep.anl.gov/askasci/chem03278.htm.*
"AMD Launches Socket F and AM2 Opterons," Aug. 2006, Tom's Hardware Guide, http://www.tomshardware.com/picturestory/21-2-amd-launches-socket-f-and-am2-opterons.html.*

* cited by examiner

*Primary Examiner* — Callie E Shosho
*Assistant Examiner* — Nicholas Kokkinos

(57) ABSTRACT

Methods and structures including a release mechanism for use with the formation and then separation of a multi-layered structure are provided. The methods and structures provide for a master substrate on which is formed a temperature-sensitive release layer. A releasable structure is then formed on top of the temperature-sensitive release layer. The releasable structure can be freed from the master substrate by exposing the temperature-sensitive release layer to a temperature sufficient to soften or melt of the release layer.

18 Claims, 5 Drawing Sheets

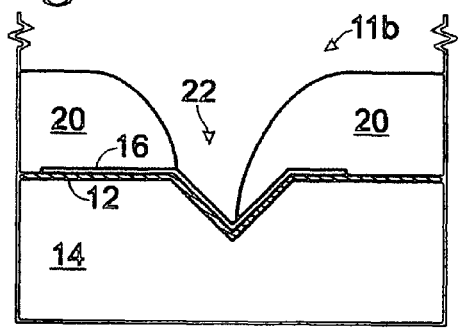
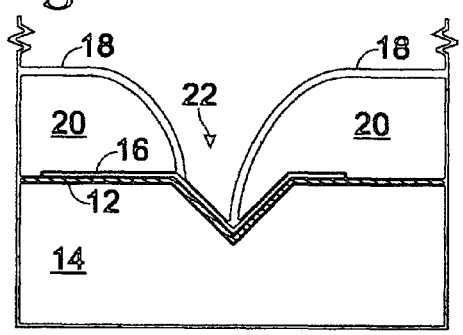
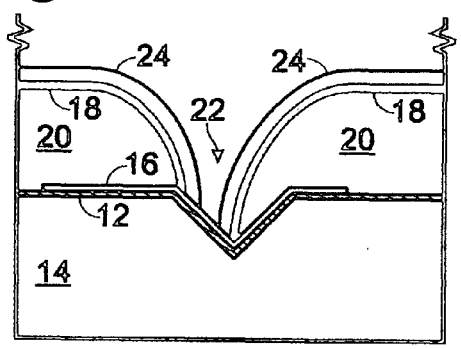
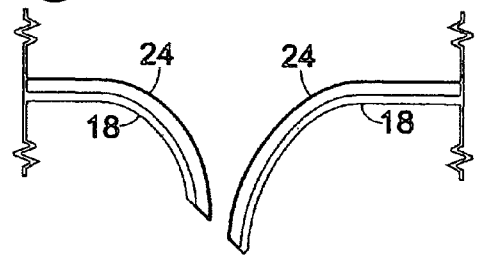
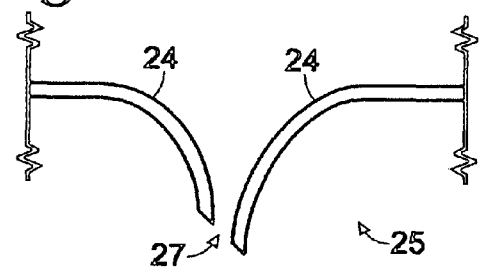

MICRONEEDLES FORMED BY ELECTROPLATING AND SELECTIVELY RELEASING TEMPERATURE SENSITIVE LAYERS

BACKGROUND

Many microfabrication methods involve electroplating layers of materials onto a plating template. According to some methods, the electroplated layers remain an integral part of the substrate in the finished product. However, for certain applications, for example, when it is desirable to reuse the template, or when integration with the template makes the finished product unsuitable for its intended use, it is desirable to remove the electroplated structure(s) from the template.

One current method involves undercutting the structure by removal of a sacrificial material layer similar to the way in which photolithographic lift-off layers are used in semiconductor processing techniques. However, when the lateral distance between areas directly exposed to the removal chemical (such as two intrusions to the base material) is substantial and the thickness of the release layer minimal, the release may be ineffective or take a disadvantageously long period of time. In addition, the chemicals used to effect the release (i.e. etch away the sacrificial layer) may adversely affect the desired resultant structure. Selective etches must be carefully chosen, and selectivity occurs in a matter of degrees, usually not just 100% or 0%.

Moreover, stress on the electroplated material during the removal process, or stress in the material as it is formed (which becomes apparent after the material is freed from it's binding support) can cause the electroplated layers to curl or otherwise alter or change in shape, possibly destroying the finished product(s). Methods to achieve plating of multiple metals include controlling stress by varying the plating bath chemistry/composition and by varying the electroplating current.

It is known to use an electrically conductive material (i.e. solder) to form an encompassing mass, which is then used to join two preformed parts together. The solder must initially be heated to its melting temperature before it can be used to join the preformed parts. Once the two parts are joined, the solder can be heated to release the two parts from each other. However, because one is dealing with a heated, amorphous, material that solidifies upon cooling, it is difficult to precisely control the shape or pattern the solder takes when the preformed parts are joined. Although one may produce a shaped column, using surface tension, from solder melted between two separated, already previously formed wettable areas (as in solder bump technology), this is an imprecise structure. A column formed in this manner does not have the top surface exposed and available for insitu formation of another shaped layer and can only accommodate a preformed part. Moreover, one must destroy the shaped solder to remove the preformed part.

Accordingly, it would be desirable to provide a mechanism for forming precise layers of materials (e.g. by electroplating) and selectively releasing some of the layers without imparting significant stress on the layers that are released. Furthermore, it would be desirable to provide a release layer which can impart specific, desired, structural characteristics to layers formed over the release layer.

SUMMARY OF THE INVENTION

According to a first embodiment, the present invention provides a fabrication method comprising forming a master substrate, forming a temperature sensitive release layer over the master substrate, forming a releasable structure over the release layer, and raising the temperature of the release layer so as to alter the release layer sufficiently that the releasable structure is released from the master substrate.

According to another embodiment, the present invention provides a fabrication method comprising providing a substrate having a desired contour, forming an electrically conductive seed layer over the substrate, forming a non-electrically conductive pattern over a portion of the seed layer containing the contour, forming a first electrically conductive layer over the seed layer and over a portion of the non-electrically conductive pattern to create a mold having a through-hole, forming a temperature sensitive release layer over the mold and forming a second electrically conductive layer over the temperature sensitive release layer.

According to still another embodiment, the present invention provides a temperature sensitive release layer that is formed between layers of materials. The layers can then be separated by heating the entire composite structure until the release layer softens or melts away entirely, thereby separating the layers without imparting substantial stress during the separation process. For example, the temperature sensitive release layer may be formed between a reusable substrate and a removable layer or structure that has been electroplated over the release layer. Furthermore, multiple release layers may be formed between multiple layers of materials in the same composite structure, allowing for a batch process formation of multiple layers of similar or dissimilar structures that can be released in a single or in multiple steps, as desired.

BRIEF DESCRIPTION OF THE DRAWINGS

FIGS. 2A-2E provide a cross sectional view of the formation of a microstructure according to another embodiment of the present invention.

DETAILED DESCRIPTION

Figure 1A:
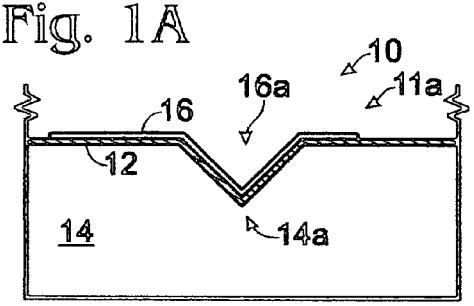
FIGS. 1A-1E provide a cross sectional view of the formation of a microstructure according to one embodiment of the present invention.

According to one embodiment, the present invention provides a fabrication method and composite structure including a selectively located and selectively removable temperature-sensitive release mechanism. The release mechanism may, for example, be a thin layer of temperature-sensitive material that is formed above a reusable master substrate and over which the structure to be released (i.e. the releasable structure) is, in turn, formed. The thin layer acts as a temperature-sensitive release layer. According to one embodiment, the temperature sensitive release layer is formed from a material that has a melting point that is lower than the other materials in the composite structure such that the releasable structure and master substrate can be heated so as to alter (e.g. soften) the release layer, thereby allowing the releasable structure to be removed from the master substrate without the structure or master substrate being subjected to substantial stress.

For the purposes of the present description, the terms "composite" or "composite structure" shall be used to refer to a multi-layered composition of matter that includes a temperature sensitive release layer sandwiched between a master substrate and a releasable structure.

The terms "releasable structure" or "releasable layer" shall refer to one or more layers of material which, when the release layer is sufficiently heated, are freed from the composite. Examples of releasable structures include, but are not limited to, (micro)needles, sheets of (micro)needles, (micro)plungers, sheets of (micro)plungers, and/or any of the above with attached molding.

Furthermore, the term "master substrate" shall be used to refer to a single or multi-layered composition of matter that serves as a base and/or template for the formation of the releasable structure. Typically, a temperature sensitive release layer will be formed between the master substrate and the releasable structure. A master substrate may comprise some or all of the following layers: a base layer such as, e.g., a mandrel; an electrically conductive seed layer; a non-conductive layer; a mold; and/or other layers, as desired or required.

As will be described in greater detail below, the master substrate may have a planar or non-planar exposed surface (i.e. the surface on which additional layers may be formed) and may include regular or irregular structures or surface variations as desired. According to some embodiments, some or all of the master substrate may be reusable.

Additionally, for the purposes of the present disclosure, the term "layer," whether or not it is preceded with the modifier "a" may contain one or more components or materials. Accordingly, while the disclosure may make reference to "a layer" being formed or provided, the "layer" being formed or provided may, in fact, comprise one, two, or more layers of the same or different materials.

The term "micro" may be used in the present disclosure to modify various other words such as in the terms "microfabrication," "microstructure," etc. According to the present disclosure, the term "micro" is used to describe an item having at least one dimension on the micron (or smaller) scale. Of course it will be appreciated that while methods described (and the structures formed thereby) in the present disclosure may be used to form structures on the micron scale, they may also be used to form large structures.

According to a first embodiment, a master substrate having an exposed surface is provided. A temperature-sensitive release layer is then formed over the exposed surface of the master substrate, thereby providing a new exposed surface. A releasable structure is then formed over the exposed surface of the temperature sensitive release layer. When it is desirable to remove the releasable structure, the temperature sensitive release layer is exposed to heat sufficient to soften or melt the release layer, thereby freeing the releasable structure from the master substrate and allowing the releasable structure to be removed from the master substrate without imparting substantial stress to the releasable structure.

According to one embodiment, while the temperature-sensitive material may be subjected to some heat during the formation process, the temperature to which it is subjected is significantly less than the melting temperature of the material being used to form the temperature-sensitive release layer.

According to another embodiment, the exposed surface of the master substrate may provide an intentionally shaped, non-planar topography. If the master substrate provides a non-planar topography, the release layer is typically formed in a precise or careful manner so as to substantially mimic the topography of the master substrate.

Once the temperature sensitive release layer is softened or melted, any suitable method or mechanism for removing the releasable structure may be employed. For example, the composite structure may be placed on a hot plate for a time sufficient to raise both the master substrate and the releasable structure to the melting temperature of the material used to form the release layer. The releasable structure may then be removed using any suitable technique including, but not limited to, mechanical peeling of the structure by turning the structure to allow gravity to remove the releasable structure, or by using vacuum suction.

From the above description, it should be understood that in contrast to soldering, where two preformed parts are joined together by an amorphous, randomly shaped material whose final form is determined by surface tension and which material must first be raised to its melting temperature before it can join the parts together, the present disclosure provides a temperature sensitive release layer that, according to various embodiments, can be formed as part of a step-wise process as one of several layers in a multi-layered composite structure, does not need to be raised to its separation temperature during formation, and/or can be formed in precise locations to mimic, provide, or impart a precise, desired, shape that is not limited in its final form by surface tension.

The material selected to form the temperature sensitive release layer may be chosen based on its ability to provide a compatible melting temperature low enough not to adversely affect surrounding materials yet high enough to coexist throughout the fabrication process. By "adversely affect" it is meant that the surrounding structure and/or materials are altered in such a way that they are no longer suitable for their intended purpose. In addition, if the material to be formed over the temperature sensitive release material is to be formed via the process of electroplating, the material selected to form the temperature-sensitive release layer may be chosen based upon its ability to conduct, in order to provide the electrical conductivity needed for plating.

Non-limiting examples of materials that are suitable for electroplating include silver (melting point of 960.8° C.), copper (melting point of 1083° C.) and gold (melting point of 1063° C.). Accordingly, one example of a material that would be suitable for use as a temperature sensitive release layer with any of the above materials is tin (Sn), which is sufficiently conductive and has a melting point at 231° C. Another suitable material is Indium (In), which is also sufficiently conductive and has a melting point at 156° C. It should be noted that the material(s) used need not be pure metals and may include alloys with different characteristics.

It will be understood that the temperature-sensitive release layer may be used in a wide variety of applications and to form any number of releasable structures. Non-limiting examples of the use of a temperature sensitive release layer to form various parts including solid microneedles, hollow microneedles, and solid microplungers are described below. However, it will be understood that such disclosure is provided only to show an example of some of the releasable structures and parts that could be formed and some of the methods that could be employed using the temperature sensitive release layer and that various other releasable structures and parts could be formed using the materials and methods described. Moreover, it will be appreciated that numerous structural variations, alterations, and modifications are possible using the methods and materials provided in the present disclosure. Furthermore, it should be understood that methods and structures that omit some of the described steps or layers and/or add additional non-described steps or layers may be employed without departing from the scope of the present disclosure.

According to one embodiment, the present disclosure provides microneedles and methods for producing the same. Referring to FIGS. 1A-1D, a cross-sectional view of a composite structure 10 is shown. In FIG. 1A, a master substrate 11a includes a first layer, which may take the form of a mandrel 14, on which has been formed an electrically conductive seed layer 12 and a non-conductive pattern 16. It can be seen that while the non-conductive pattern has been formed over a portion of the seed layer, some of the seed layer remains exposed.

Mandrel 14 may be constructed from semiconductor material such as silicon, a nonconductive material such as glass, a metal such as stainless steel or aluminum, a pre-molded plastic, or any other suitable material.

As shown, mandrel 14 may have a non-planar upper surface. In the depicted embodiment, mandrel 14 includes a shaped contour or well region 14a. As stated above, a master substrate and, correspondingly, mandrel 14 may include other types of uniform or non-uniform, planar, non-planar, regular or irregular structures, and/or any other surface variations. Accordingly, mandrel 14 may include any number of raised or depressed regions of any suitable shape or size, as desired. For example, mandrel 14 may be given a surface treatment using silane ($SiH_4$) and nanoparticles to produce increased surface area or surface roughness on which the seed layer 12 could be formed. This same surface could be patterned by lithographic means or imprinted, with or without any additional intervening layers.

Seed layer 12 may be a layer of chrome, stainless steel, tantalum, gold, or any other suitable conductive material(s) and may be formed by sputtering or any other suitable technique(s) including electroless plating after surface activation. Alternatively or additionally, the seed layer may be a bi- or multi-layer formed from two or more materials. For example, the seed layer may be formed from layers of chrome and stainless steel or layers of tantalum and gold. It should be noted that other materials such as conductive polymers may be used to form seed layer 12. As shown in the depicted embodiment, seed layer 12 may be formed so as to substantially reproduce the topography of the upper surface of mandrel 14. According to some embodiments, the seed layer may have a thickness of between about 500 Angstroms [50 nm] and about 200,000 Angstroms [20 μm].

Nonconductive layer 16 may be formed on the seed layer 12 and formed so as to produce a nonconductive pattern. The nonconductive layer may be formed, for example, from silicon carbide and deposited by plasma enhanced chemical vapor deposition [PECVD]. In one embodiment, patterning of the nonconductive layer may be accomplished by forming a photolithographic mask on the nonconductive layer followed by etching, or by using lithographic lift-off methods following deposition. Other suitable materials for the nonconductive pattern include, but are not limited to, photoresist, silicon nitride, and silicon oxide. In the depicted embodiment, the nonconductive pattern is deposited so as to cover the region of the formed well 14a so as to maintain the desired surface topography as shown at 16a. According to some embodiments, the nonconductive pattern may have a thickness of between about 500 Angstroms and 500,000 Angstroms [50 μm].

As formed, master substrate 11a includes an exposed upper surface that generally mimics the topography of the upper surface of mandrel 14 and comprises nonconductive pattern 16 and the portion(s) of seed layer 12 that are not covered by non-conductive pattern 16.

Figure 1B:
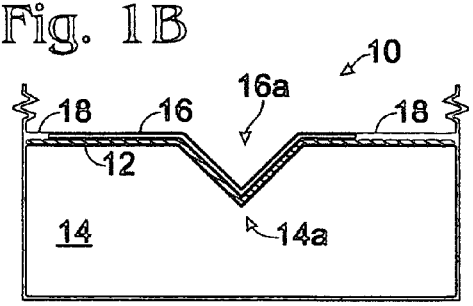
Figure 1C:
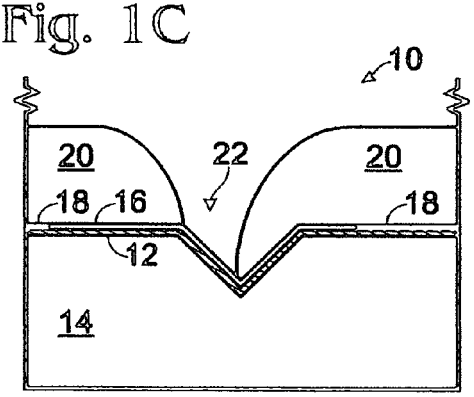

Turning to FIG. 1B, a release layer 18 may be electroplated or otherwise formed on the exposed upper surface of master substrate 11a. In the depicted embodiment, the release layer 18 is not formed over the non-conductive pattern 16. Accordingly, release layer 18 is formed in a pattern so as to substantially cover the portions of seed layer 12 that are not covered by non-conductive layer 16. Typically, release layer 18 should substantially cover seed layer 12 such that when a releasable structure is formed on top of release layer 18 (as shown in FIGS. 1B and 1C), heating of the release layer is sufficient to allow the releasable layer to detach from the master substrate without significant force.

In order to form a releasable structure having a desired shape, a mold may be formed (e.g. by electroplating) on the release layer. In the example depicted in FIGS. 1A-1E, the release layer acts as an adhesive layer between the master substrate 11a and an electroplated micromold 20, shown in FIGS. 1C-1E. The material used as a release layer may be selected based on the materials used for the master substrate, micromold, and releasable structure so as to ensure that the melting point of the release layer is substantially lower than that of the master substrate, micromold, and releasable structure. By "substantially lower" it is meant that the difference between the melting points is large enough that the entire composite can be heated to a temperature which is sufficient to cause the release layer to sufficiently soften to allow release of the structures to which it is adhered, but which temperature does not adversely affect the master substrate, micromold or releasable structure. Moreover, in an embodiment in which the releasable layer is electroplated, the release layer should be formed from a material that is sufficiently conductive to allow for additional electroplating and from a material that has adequate adhesion to neighboring layers.

For example, tin and indium adhere well to nickel and steel, are conductive, and have a lower melting point than nickel and steel. Accordingly, a seed layer may be formed from steel, a micromold material from nickel, and a release layer from tin or indium.

It will be appreciated that the precise specifications (e.g. temperature and time) that should be used in order to soften or melt the release layer sufficiently, will depend upon multiple factors including, but not necessarily limited to, the specific method used to heat the composite structure, the size (both surface area and thickness) of the composite structure and its component layers, and the materials used. For example, if a composite structure is formed from a silicon mandrel, an indium release layer and a silver releasable structure, the composite structure could be raised to the melting point of indium (156° C.) within a matter of minutes via hot plate, oven, or furnace.

According to one embodiment, the thickness of the temperature-sensitive release layer may be between 50 Angstrom [5 nm] and 200,000 Angstrom [20 μm]. It will be appreciated by those skilled in the art that the melting point of thin layers is different from that of bulk material.

Turning to FIG. 1C, micromold 20 may be formed by plating (or otherwise forming) a first metal onto seed layer 12 which as it grows will extend over a portion of nonconductive pattern 16. According to the depicted embodiment, the first metal is plated so as to maintain exposure of a portion of the nonconductive pattern, thereby forming an opening 22 in micromold 20. It can be seen that micromold 20 has been plated such that one region of micromold 20 is offset with respect to opening 22. This offset allows the process to produce releasable structures with a sharp feature, such as microneedles with a sharp tip. However, it will be appreciated that the micromold could be formed to have any desired size or shape and may expose any desired region of the nonconductive pattern in order to produce any desired structure. Accordingly, a needle or other structure could be produced having a rounded, squared-off, or any other shaped tip. Moreover, a needle or structure could be produced having a round, oval, square, or other uniform or non-uniform shaped opening. Furthermore, the structure produced may not be a needle and may not have a "tip" at all.

Figure 1D:
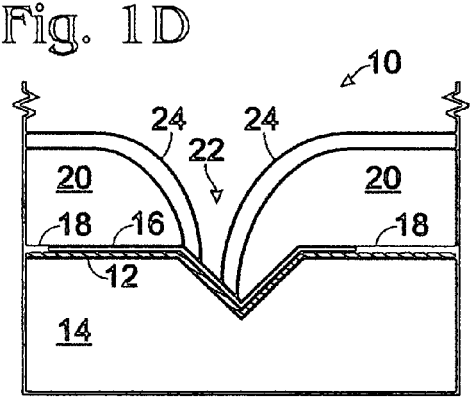

In FIG. 1D, a second material, is plated (or otherwise formed) over the micromold 20. According to the particular depicted embodiment, the plating thickness of the second metal may be controlled so as to form a plated coating on the sidewall of the opening 22, thereby forming a hollow structure or part 24, such as a hollow microneedle. Of course it will be appreciated that if it were desired to form either a closed hollow structure or closed solid structure (e.g. a part not having an opening or through-hole), such as a solid microneedle, the plating parameters (or other means of formation) could be adjusted so that the second plated (or otherwise formed) material could cover or even completely fill-in opening 22.

Part 24 may be constructed from a variety of metals or other suitable materials depending on the intended use. In the instance of the part taking the form of a microneedle intended for medical applications, the metal part 24 may be made of palladium, silver, gold, nickel, brass, bronze, or alloys thereof. According to one embodiment, the thickness of the second material, when plated, may be between about 5 µm to about 500 µm.

It should be appreciated that part 24 may be formed from materials other than metal. For example, those of skill in the art will be familiar with conductive polymers. Accordingly, conductive polymers that have or are capable of having characteristics that are desirable in the final product may be used in addition to or in lieu of metal. Generally, any material having or capable of achieving the desired post-process properties may be used. For example, if the final product is to be a needle, the material used to form part 24 may be selected based on its capability of achieving the hardness, stiffness, compliance, strength, sharpness, and/or any other property required to achieve the desired size, degree of needle penetration, comfort, etc.

It will still further be appreciated that a suitable conductive polymer or other material may be used instead of, or in addition to, any of the presently-described layers in the electroplated composition, so long as the polymer has or is capable of having the desired properties.

Figure 1E:
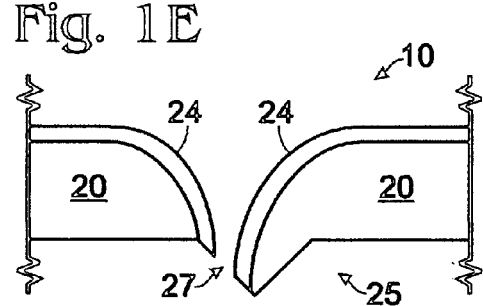

In FIG. 1E, the composite structure in FIG. 1D has been heated to a suitable temperature to melt release layer 18, thereby freeing the releasable structure 25 which has been formed thereon. As shown, in this example, the releasable structure 25 includes both micromold 20 and part 24. Moreover, because opening 22 remained unfilled throughout the process, it can be seen that the releasable structure includes a through-hole 27.

It will be appreciated that according to some embodiments master substrate 11a may be reusable. Accordingly, if desired, once the releasable structure(s) have been freed from the reusable master substrate, a new release layer may be formed over the reusable master substrate and the process repeated, as desired.

FIGS. 2A-2E depict an alternate method for forming a releasable structure. In FIG. 2A, master substrate 11b comprises a metal-containing seed layer 12, a mandrel 14, a nonconductive pattern 16 and a micromold 20. As shown, metal-containing seed layer 12 is formed on top of a mandrel 14 and a nonconductive pattern 16 is formed over seed layer 12. In this embodiment, the micromold 20 is formed directly over seed layer 12 and extends over a portion of nonconductive pattern 16. Accordingly, the exposed upper surface of master substrate 11b includes the upper (i.e. exposed) surface of micromold 20 and the portion(s) of nonconductive pattern 16 that were not covered by micromold 20.

Turning to FIG. 2B, a temperature sensitive release layer 18 is then formed [as a non-limiting example, by plating] in a pattern above the master substrate by controlling the thickness of the release layer so as to maintain opening 22. According to one embodiment, the temperature-sensitive release layer may have a thickness of between about 50 Angstroms (5 nm) and about 200,000 Angstroms [20 µm].

In FIG. 2C, a conductive layer is plated over release layer 18 so as to form hollow releasable structure, or part 24. Again it will be appreciated that should it be desirable to form a solid part (i.e. a part not having a through-hole), the conductive layer may be plated or otherwise formed so as to allow it to fill some or all of opening 22. It should be appreciated that while the description makes frequent reference to metal as the deposited material and describes the method in which the metal is deposited as plating, the deposited material may be a material other than metal and, further, the deposited material may be deposited using means other than plating.

In FIG. 2D, the composite in FIG. 2C has been heated to a suitable temperature to melt release layer 18, thereby releasing part 24 from micromold 20. As shown, extraneous release layer may remain adhered to part 24 and such extraneous material may be removed, for example, by additional heating or by selective etching. FIG. 2E depicts the released hollow metal part freed from any other materials or structures. Accordingly, because the release layer 18 was formed between micromold 20 and part 24, it can be seen that in this embodiment, the releasable structure 25 consists only of part 24, which includes a through-hole 27.

Again, it will be appreciated that according to some embodiments master substrate 11b may be reusable. Accordingly, if desired, once the releasable structure(s) have been freed from the reusable master substrate, a new release layer may be formed over the reusable master substrate and the process repeated, as desired.

The methods and structures described in the present disclosure may be used to build layers of structures on top of each other, with each structural layer being separated by a temperature-sensitive release layer. Such a system allows for the formation of significantly more structures using blanket depositions or blanket forming techniques, producing a significant saving in both time and cost. It should be appreciated that a given layered, or nested, structure may or may not follow some or all of the contours of the layer beneath it.

Figure 3A:
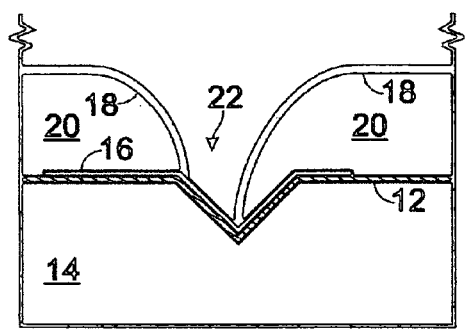
FIGS. 3A-3E provide a cross sectional view of the formation of two different microstructures according to yet another embodiment of the present invention.

FIGS. 3A-3E provide yet another method according to the present invention. In FIG. 3A a metal-containing seed layer 12 is formed on top of a mandrel 14. A nonconductive pattern 16 is formed on top of seed layer 12. In this embodiment, the micromold 20 is formed directly on seed layer 12 and extends over a portion of nonconductive pattern 16. The temperature sensitive release layer 18 is then patterned on top of the micromold 20. Again, the thickness of the release layer may be controlled so as to maintain the desired size of opening 22.

Figure 3B:
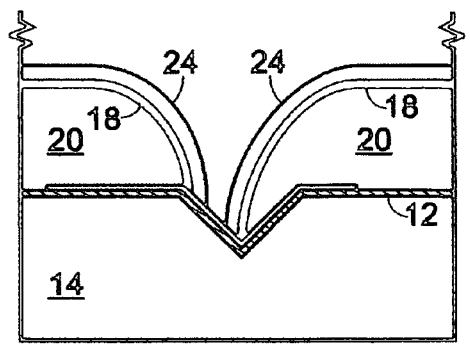

In FIG. 3B, a metal or other suitable material is formed over release layer 18 so as to create a releasable structure 24 having a through-hole 25. According to some embodiments, hollow releasable structure 24 may be a hollow microneedle.

Figure 3C:
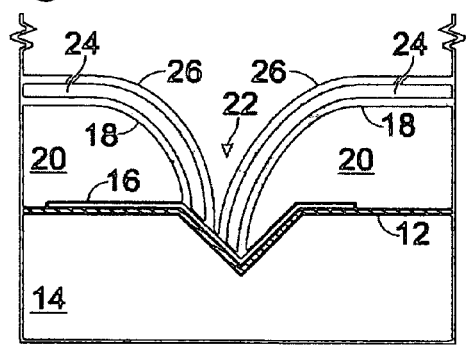

In FIG. 3C, a second temperature sensitive release layer 26 is formed over hollow releasable structure 24.

Figure 3D:
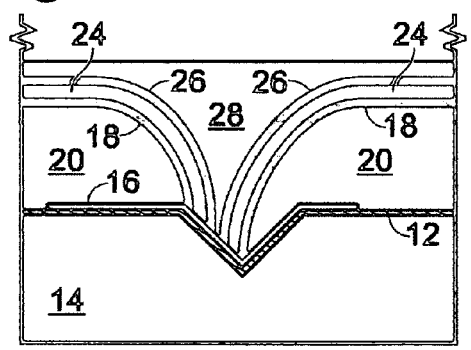

In FIG. 3D, a metal or other suitable material is formed over release layer 26 so as to form a solid releasable structure 28, which is sized to fit inside of, or be received by, hollow releasable structure 24. According to some embodiments, solid releasable structure 28 may be a solid plunger or microneedle. It will be appreciated that the size of the opening in hollow releasable structure 24 and the size of the tip of solid releasable structure 28 may be altered, as desired, by changing the size of the opening 22 formed by micromold 20 and/or the thicknesses of the various layers that are formed over the micromold.

Figure 3E:
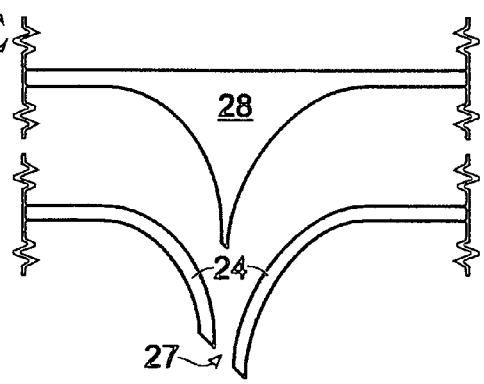

In FIG. 3E, the composite structure in FIG. 3D has been heated to a suitable temperature to melt release layers 18 and 26, thereby freeing hollow releasable structure 24 and solid releasable structure 28. As shown, because no metal was plated over opening 22, releasable structure 24 includes a through-hole 27.

Figure 4A:
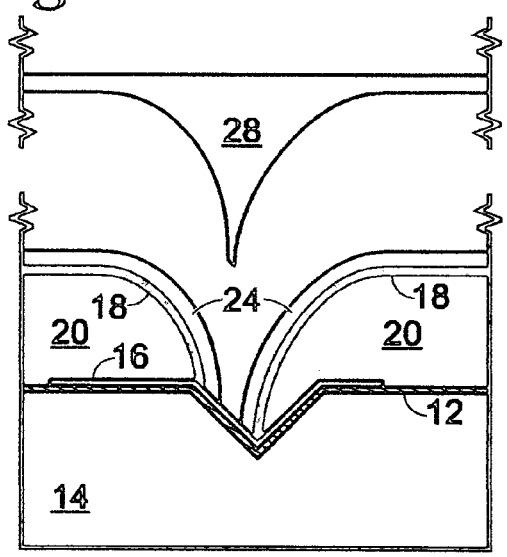
FIGS. 4A-4B provide a cross sectional view of the formation of nested structures according to still another embodiment of the present invention.
Figure 4B:
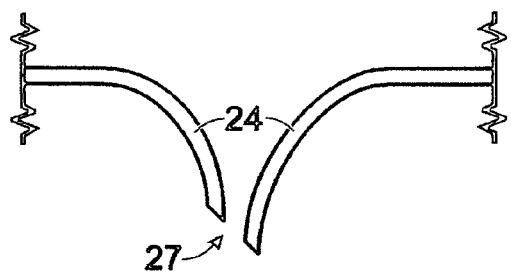

FIGS. 4A and 4B depict a slight alteration to the method shown in FIGS. 3A-3E. In this method, release layers 18 and 26 are formed from different materials having different melting points. For example, release layer 26 is formed from indium and release layer 18 is formed from tin. Accordingly, in FIG. 4A, the composite structure has been heated to the point in which release layer 26 softens or melts sufficiently to free solid releasable structure 28, while hollow releasable 24 remains adhered to micromold 20 via release layer 18. In FIG. 4B, the resulting composite structure is heated to a temperature sufficient to free hollow releasable structure 24.

Figure 5A:
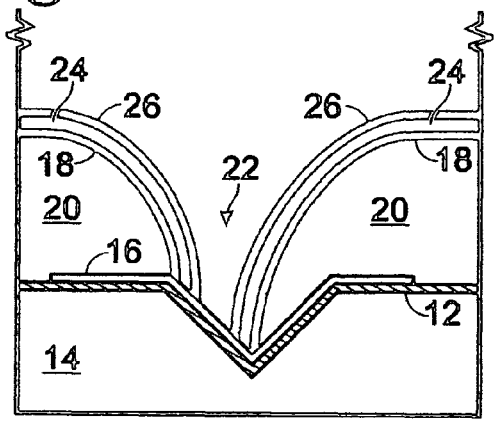
FIGS. 5A-5C provide a cross sectional view of the formation of different microstructures according to another embodiment of the present invention.
Figure 5B:
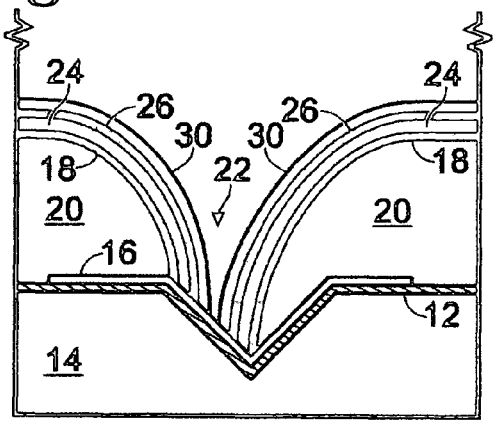
Figure 5C:
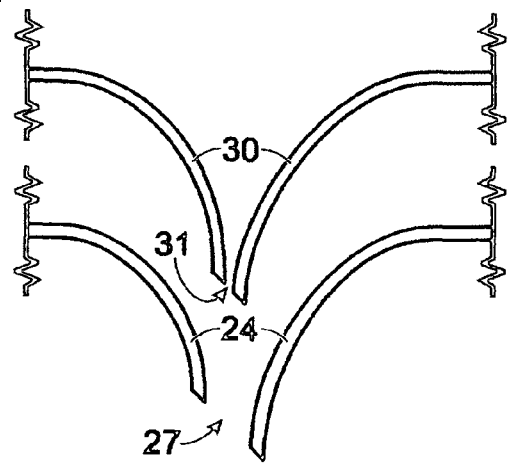

FIGS. 5A-5C depict another method of forming nested parts. In FIG. 5A, a metal-containing seed layer 12 is formed over mandrel 14. A nonconductive pattern 16 is formed on top of seed layer 12. Micromold 20 is formed directly on seed layer 12 and extends over a portion of nonconductive pattern 16. The temperature sensitive release layer 18 is then formed over micromold 20. The thickness of release layer 18 is controlled so as to maintain opening 22. A metal, or other suitable material, layer is formed over release layer 18 so as to form hollow releasable structure 24. A second release layer 26 is formed over hollow releasable structure 24. As with release layer 18, the thickness of release layer 26 can be controlled so as to maintain opening 22.

In FIG. 5B, another metal, or other suitable material, layer is formed over release layer 26 to form a second hollow releasable structure 30 having opening 31. Again, it will be appreciated that the size of the openings 27, 31 of each of the nested parts may be altered, as desired, by controlling the size of opening 22 created by micromold 20 and/or the thicknesses of the various layers. It should be appreciated that additional nested parts may be formed on top of each other so long as there is a sufficiently sized opening 22 to allow for an additional part of the desired shape. Moreover, it should further be appreciated that a solid part, such as a solid needle, or plunger, may be included as a layer, as desired.

In FIG. 5C, the composite structure has been heated sufficiently to melt the release layers and free structures 24 and 30. It will be appreciated that the release layers may be formed from the same or different materials. If different materials having different melting temperatures are used, as in the embodiment shown with respect to FIGS. 4A and 4B, the various nested structures could be released individually, for example, to allow for size differentiation.

It will be appreciated that all of the above structures and methods can be adapted to form an array of fabricated structures. In varying embodiments, the steps and structures are the same, except that a single master substrate may or may not contain numerous identical or different desired surface modifications and/or an array of nonconductive varied or unvaried patterns may be formed on the seed layer. Moreover, the various layers that are discussed as being formed, (e.g. via plating, depositing, or other suitable techniques), may be formed using blanket techniques. Furthermore, the structures may be released as part of one or more sheets of structures which then may or may not be subjected to additional downstream processing.

It should further be appreciated that while much of the above-description is directed to the formation of hollow and solid microneedles and plungers, the above-described techniques may be employed to produce a wide variety of structures including, but not limited to, various three-dimensional structures, flat sheets, plates with through-holes, etc. and such structures are considered as falling within the scope of the present disclosure.

While the above structures and methods have been described and illustrated in such as way as to show the use of multiple layers of materials it will be understood that it may not be necessary to include every depicted or described layer in any given embodiment. For example, some desired structures may not require the use of a non-conductive pattern and in such a case, the non-conductive pattern may be omitted from the process, without departing from the scope of the present disclosure. Alternatively or additionally, additional temperature-sensitive layers may be included in various places in the composite structure to allow for separation of the composite structure and any desired position.

Accordingly, while certain embodiments have been described herein in connection with the drawings, these embodiments are not intended to be exhaustive or limited to the precise form disclosed. Those skilled in the art will appreciate that obvious modifications and variations may be made to the disclosed embodiments without departing from the subject matter and spirit of the invention as defined by the appended claims.

What is claimed is:

1. A fabricated composite structure, comprising:
   a master substrate that serves as a template for forming a microneedle, the master substrate comprising:
   a first layer having a surface and a topography; and
   an electrically conductive seed layer formed over the surface of the first layer and formed so as to mimic the topography of the first layer;
   a micromold formed over the electrically conductive seed layer, the micromold having an inner facing surface with respect to the surface of the first layer of the master substrate and an opposed outer facing surface with respect to the surface of the first layer of the master substrate, a desired shape along the outer surface that defines a shape of the formed microneedle, and a through-hole defined between the outer facing surface and the inner facing surface;
   a temperature sensitive layer conforming to and in contact with at least a portion of the inner facing or the outer facing surfaces of the micromold; and
   the microneedle formed of a releasable layer established over the outer facing surface such that the microneedle mimics the desired shape of the outer facing surface, the microneedle having an opening therethrough having been defined by the through-hole of the micromold;
   wherein, when the temperature sensitive layer is heated to a suitable temperature, at least the microneedle is released from the master substrate.

2. The fabricated composite structure of claim 1 where the topography of the first layer is non-planar.

3. The fabricated composite structure of claim 1 wherein the micromold is electrically conductive.

4. The fabricated composite structure of claim 1, further comprising:
a second temperature sensitive layer formed over and covering the releasable layer; and
a second releasable layer formed over the second temperature sensitive layer.

5. The fabricated composite structure of claim 1 wherein the temperature sensitive layer is tin.

6. The fabricated composite structure of claim 1 wherein the temperature sensitive layer is indium.

7. The fabricated composite structure of claim 1 wherein the temperature sensitive layer is a polymer.

8. The fabricated composite structure of claim 1 wherein the temperature sensitive layer has a thickness of between 50 Angstroms and 200,000 Angstroms.

9. A fabricated composite structure, comprising:
a master substrate that serves as a template for forming a releasable part, the master substrate comprising:
a first layer having a surface and a topography; and
an electrically conductive seed layer formed over the surface of the first layer and formed so as to mimic the topography of the first layer;
a mold formed over the electrically conductive seed layer, the mold having an inner facing surface with respect to the surface of the first layer of the master substrate and an opposed outer facing surface with respect to the surface of the first layer of the master substrate, a desired shape along the outer surface, and a through-hole defined between the outer facing surface and the inner facing surface;
a temperature sensitive layer conforming to and in contact with at least a portion of the inner facing or the outer facing surfaces of the mold; and
the releasable part formed of a releasable layer established over the outer facing surface such that the part mimics the desired shape of the outer facing surface;
wherein, when the temperature sensitive layer is heated to a suitable temperature, at least the releasable part is released from the master substrate;
wherein the temperature sensitive layer is positioned between a portion of the electrically conductive seed layer and the inner facing surface of the mold, and wherein the releasable layer is established directly on and in contact with the outer facing surface having the desired shape.

10. The fabricated composite structure of claim 9 wherein the master substrate further comprises a non-conductive pattern formed between the inner facing surface of the mold and a portion of the electrically conductive seed layer such that a portion of the non-conductive pattern is exposed through the through-hole in the mold.

11. The fabricated composite structure of claim 10 wherein the temperature sensitive layer covers any portion of the electrically conductive seed layer that is not covered by the non-conductive pattern.

12. A fabricated composite structure, comprising:
a master substrate that serves as a template for forming a releasable part, the master substrate comprising:
a first layer having a surface and a topography; and
an electrically conductive seed layer formed over the surface of the first layer and formed so as to mimic the topography of the first layer;
a mold formed over the electrically conductive seed layer, the mold having an inner facing surface with respect to the surface of the first layer of the master substrate and an opposed outer facing surface with respect to the surface of the first layer of the master substrate, a desired shape along the outer surface, and a through-hole defined between the outer facing surface and the inner facing surface;
a temperature sensitive layer conforming to and in contact with at least a portion of the inner facing or the outer facing surfaces of the mold; and
the releasable part formed of a releasable layer established over the outer facing surface such that the part mimics the desired shape of the outer facing surface;
wherein, when the temperature sensitive layer is heated to a suitable temperature, at least the releasable part is released from the master substrate, wherein the temperature sensitive layer is positioned on and conforms to the entire outer facing surface having the desired shape, and wherein the releasable layer is established on the temperature sensitive layer.

13. The fabricated composite structure of claim 12 wherein the master substrate further comprises a non-conductive pattern formed between a portion of the electrically conductive seed layer and the inner facing surface of the mold such that the non-conductive pattern is exposed through the through-hole in the mold.

14. The fabricated composite structure of claim 13 wherein the releasable layer is formed on the temperature sensitive layer so that at least a portion of the non-conductive pattern remains exposed.

15. The fabricated composite structure of claim 13 wherein the releasable layer is formed over the temperature sensitive layer so as to cover the non-conductive pattern.

16. The fabricated composite structure of claim 12, further comprising:
a second temperature sensitive layer formed over and covering the releasable layer; and
a second releasable layer formed over the second temperature sensitive layer.

17. The fabricated composite structure of claim 16 wherein the first and second temperature sensitive layers are formed of different materials having different melting points.

18. The fabricated composite structure of claim 17 wherein the first temperature sensitive layer is tin and wherein the second temperature sensitive layer indium.

* * * * *